US010413637B2

(12) United States Patent
Bourdon et al.

(10) Patent No.: US 10,413,637 B2
(45) Date of Patent: *Sep. 17, 2019

(54) COMPOSITION COMPRISING HYALURONIC ACID AND MEPIVACAINE

(71) Applicant: Teoxane, Geneva (CH)

(72) Inventors: Francois Bourdon, Gaillard (FR); Stephane Meunier, Thoiry (FR)

(73) Assignee: TEOXANE, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,598

(22) Filed: Feb. 22, 2019

(65) Prior Publication Data
US 2019/0184065 A1 Jun. 20, 2019

Related U.S. Application Data

(60) Continuation of application No. 15/895,220, filed on Feb. 13, 2018, which is a continuation of application No. 15/705,809, filed on Sep. 15, 2017, now Pat. No. 9,925,309, which is a continuation of application No. 15/044,236, filed on Feb. 16, 2016, now Pat. No. 9,789,226, which is a division of application No. 13/954,360, filed on Jul. 30, 2013, now Pat. No. 9,421,198.

(51) Int. Cl.
*A61L 27/54* (2006.01)
*A61Q 19/08* (2006.01)
*A61K 31/728* (2006.01)
*A61K 31/16* (2006.01)
*A61K 8/49* (2006.01)
*A61K 31/167* (2006.01)
*A61L 27/20* (2006.01)
*A61L 27/12* (2006.01)
*A61K 9/00* (2006.01)
*A61K 8/24* (2006.01)
*A61K 8/73* (2006.01)
*A61K 31/445* (2006.01)
*A61K 31/451* (2006.01)
*A61K 47/02* (2006.01)

(52) U.S. Cl.
CPC .............. *A61L 27/54* (2013.01); *A61K 8/24* (2013.01); *A61K 8/4926* (2013.01); *A61K 8/735* (2013.01); *A61K 9/0019* (2013.01); *A61K 9/0024* (2013.01); *A61K 31/16* (2013.01); *A61K 31/167* (2013.01); *A61K 31/445* (2013.01); *A61K 31/451* (2013.01); *A61K 31/728* (2013.01); *A61K 47/02* (2013.01); *A61L 27/12* (2013.01); *A61L 27/20* (2013.01); *A61Q 19/08* (2013.01); *A61K 2800/524* (2013.01); *A61K 2800/75* (2013.01); *A61K 2800/91* (2013.01); *A61L 2300/204* (2013.01); *A61L 2300/402* (2013.01); *A61L 2400/06* (2013.01)

(58) Field of Classification Search
CPC ........ A61K 8/24; A61K 8/4926; A61K 8/735; A61K 31/728; A61K 31/167; A61K 31/451; A61K 31/445; A61K 31/16; A61K 9/0024; A61K 9/0019; A61K 47/02; A61L 27/54; A61L 27/20; A61L 27/12
See application file for complete search history.

(56) References Cited

U.S. PATENT DOCUMENTS

| | | |
|---|---|---|
| 8,357,795 B2 | 1/2013 | Lebreton |
| 8,450,475 B2 | 5/2013 | Lebreton |
| 8,822,676 B2 | 9/2014 | Lebreton |
| 9,089,518 B2 | 7/2015 | Lebreton |
| 9,421,198 B2 | 8/2016 | Bourdon et al. |
| 9,498,562 B1 | 11/2016 | Bourdon et al. |
| 9,789,226 B2 | 10/2017 | Bourdon et al. |
| 2005/0136122 A1 | 6/2005 | Sadozai et al. |
| 2006/0122147 A1 | 6/2006 | Wohlrab |
| 2010/0028437 A1 | 2/2010 | Lebreton |
| 2011/0171286 A1 | 7/2011 | Cecile et al. |
| 2012/0004292 A1 | 1/2012 | Villette |
| 2013/0123210 A1 | 5/2013 | Liu et al. |
| 2014/0005140 A1 | 1/2014 | Piron et al. |
| 2014/0088037 A1 | 3/2014 | Bon Betemps et al. |
| 2014/0170251 A1 | 6/2014 | Trumbore et al. |

(Continued)

FOREIGN PATENT DOCUMENTS

| | | | |
|---|---|---|---|
| FR | 2979539 A1 | 3/2013 | |
| WO | 2004032943 A1 | 4/2004 | |

(Continued)

OTHER PUBLICATIONS

International Search Report for PCT/IB2014/063603 dated Nov. 21, 2014 (4 pages).

(Continued)

*Primary Examiner* — Jonathan S Lau
(74) *Attorney, Agent, or Firm* — Shumaker, Loop & Kendrick, LLP

(57) ABSTRACT

A sterile composition for intraepidermal, intradermal, and/or subcutaneous administration including an effective amount of hyaluronic acid or a salt thereof, the effective amount of hyaluronic acid or salt thereof ranging from 1 to 3 wt % of the overall weight of the sterile composition, mepivacaine or a salt thereof as a first anesthetic agent at a concentration ranging from 0.05 to 3 wt % of an overall weight of the sterile composition, and a balanced salt solution in which the sterile composition exhibits greater stability over time and/or during heat treatment resulting in sterilization in comparison to the same composition having lidocaine as the anesthetic agent instead of mepivacaine.

19 Claims, No Drawings

(56) References Cited

U.S. PATENT DOCUMENTS

| | | |
|---|---|---|
| 2018/0021480 A1 | 1/2018 | Bourdon et al. |
| 2018/0169304 A1 | 6/2018 | Bourdon et al. |

FOREIGN PATENT DOCUMENTS

| | | |
|---|---|---|
| WO | 2010015900 A1 | 2/2010 |
| WO | 2010015901 A1 | 2/2010 |
| WO | 2010131175 A1 | 11/2010 |
| WO | 2010136594 A2 | 12/2010 |
| WO | 2011086458 A1 | 7/2011 |
| WO | 20120104419 A1 | 8/2012 |
| WO | 20130092860 A2 | 6/2013 |
| WO | 2014165113 A1 | 10/2014 |

OTHER PUBLICATIONS

Written Opinion for PCT/IB2014/063503 dated Feb. 5, 2015 (6 pages).
IPRP for PCT/IB2014/063503 dated Feb. 5, 2015 (7 pages).
Article 34 Amendments in PCT/IB2014/063503 (7 pages).
Rule 132 Declaration of Frencois Bourdon (Iinventor), submitted by Applicants in parent case U.S. Appl. No. 15/044,236 on Jun. 7, 2017 (Year:2017).
Wahl, G., Journal of Cosmetic Derrmatology. 2008, 7, p. 298-303.
Gadsden, et al. "The effect of mixing 1.5% mepivacaine and 0.5% bupivacaine on duration of analgesia and latency of block onset in ultrasound-guided interscalene block." Anesth. Analg. Feb. 2011; 112(2): 471-6; (Abstract Only provided).
Prendergast & Shiffman, eds. Aesthetic Medicine (Springer Berlin Heidelberg, 2012) (chapter 9, Local regional anesthesia. 87-91).
Duranti et al., Dermatol. Surg., 1998, 24, p. 1317-1325.
Collins et al., Arch. Surg., 1962, 84(6), p. 680-685.
Hobeich P. et al., "A Prospective, Randomized, Double-blind Comparison of the Injection Pain and Anesthetic Onset of 2% Lidocaine with 1:100,000 Epinephrine Buffered with 5% and 10% Sodium Bicarbonate in Maxillary Infiltrations." J. Endod. May 2013; 39(5): 597-9.
Farley JS, Hustead RF, Becker KE. "Diluting lidocaine and mepivacaine in balanced salt solution reduces the pain of intradermal injection." Regional Anaesthesia. 1994; 19:48-51.
Definition of Prevent, Oxford English Dictionary Online, http://dictionary.oed.com/, accessed online Mar. 27, 2010, especially definition 9a, at p. 2.
Japanese Patent Office Action issued for JP2016-530646 with English translation dated Apr. 3, 2018.
T. Iannitti et al.; Short Review on Face Rejuvination Procedures: Focus on Preoperative Antiseptic and Anesthetic Delivery by Jet Peel-3 (A High Pressure Oxygen Delivery Device); Minerva Chirurgica; vol. 66, Suppl. I; No. 3; Guigno, 2011 (11 pp.).

COMPOSITION COMPRISING HYALURONIC ACID AND MEPIVACAINE

FIELD OF INVENTION

The present invention relates to the field of sterile and injectable compositions comprising hyaluronic acid or a salt thereof, and especially soft tissue filler compositions, for in particular the augmentation and/or repair of soft tissue, including periodontal tissue, and especially for treatment of defects and imperfections of keratin materials, like the skin. The invention is also directed to related methods.

BACKGROUND OF THE INVENTION

There have been efforts to develop compositions useful to correct defects in skin such as scars and wrinkles or to augment the tissue of a subject in order to improve the appearance of the skin, particularly facial skin. The principal method employed to correct such defects involves injecting a filler composition into the dermal layer of the skin proximate to the effect or desired tissue augmentation.

The hyaluronic acid is the major component of the extracellular matrix (ECM). It is thus found in large quantities mainly in the skin. It is also the major physiological component of the articular cartilage matrix and is particularly abundant in synovial fluid.

Accordingly, the hyaluronic acid, in its acid or salt form, is a biomaterial largely used as injectable filler material for tissue engineering application and especially for augmentation of dermal tissue or other soft tissue like gingival tissue.

Hyaluronic acid is a linear non-sulfated glycosaminoglycan composed of repeating units of D-glucuronic acid and N-acetyl-D-glucosamine (Tammi R., Agren U M., Tuhkanen A L., Tammi M. Hyaluronan metabolism in skin. Progress in Histochemistry & Cytochemistry 29 (2): 1.-81, 1994).

In the skin, hyaluronic acid is primarily synthesized by dermal fibroblasts and epidermal keratinocytes (Tammi R., cited above). Through its residues bearing a negative charge, hyaluronic acid acts as a water pump for maintaining the elasticity of the skin.

In addition, the ECM is a dynamic structure with a structural and regulatory role for the tissues. The ECM is composed of collagen and elastin and also fundamental substance, mainly water, minerals and proteoglycans. This matrix gives to the skin its turgor and mechanical properties of firmness, elasticity and tone.

Regarding the skin, it is noticed that, with age, the amount of hyaluronic acid and its degree of polymerization decreases, resulting in a decrease in the amount of water retained in the connective tissue.

Meanwhile, ECM components are degraded, mainly by endopeptidase type enzymes called matrix metalloproteinases or MMPs.

Finally, decreases in cellular defenses increase damage and disorders induced by external stresses such oxidative stress.

The skin is then subjected to an aging process leading to the appearance of defects and blemishes of keratinous substances, in particular of the skin.

In the field of wrinkle fillers, gels consisting mainly of hyaluronic acid, the case arising chemically crosslinked, are injected intradermally to fill the depression dug by the ride. The crosslinking can increase the persistence of the product within the dermis. Such gels based on hyaluronic acid, if necessary crosslinked, allow a reduction of wrinkles by the mechanical effect of the filler resulting from the vacuum skin wrinkle.

However, it is known that the injection of such gels often produces a painful sensation for the patient, this sensation being further exacerbated more the gel is highly viscous and/or elastic.

Today, so as to overcome this technical problem, the main fillers based on hyaluronic acid are available with a local anesthetic agent to ensure greater patient comfort. This local anesthetic agent is only lidocaine, with a dosage of about 0.3%.

However, it is known that lidocaine may display the disadvantage, regarding its vasodilatory properties, to imply a too rapid absorption by the patients body and sometimes an exacerbated occurrence of hematoma which are, for obvious aesthetic reasons, to be avoided as much as possible. A solution to overcome the above-mentioned problems may consist to implement the lidocaine in association with a vasoconstrictor, in particular epinephrine (J. Endod. 2013 May; 39(5):597-9). However, the presence of a vasoconstrictor like epinephrine may require adding a preservative which isn't always inert with respect to the patient and may conduct to allergies.

Therefore, it remains a need to develop gels consisting mainly of hyaluronic acid, the case arising chemically crosslinked, which overcomes the above-mentioned technical problems of the painful sensation for the patient during the injection and which also do not involve any problem of allergies nor exacerbated occurrence of hematoma.

SUMMARY OF INVENTION

According to a first aspect, the invention relates to a method comprising at least the administering by injection to a patient in need thereof of:

(a) at least an efficient amount of hyaluronic acid or a salt thereof; and (b) at least an efficient amount of mepivacaine or a salt thereof as anesthetic agent, said mepivacaine being administered before or concurrently with the hyaluronic acid.

According to specific aspect, the method of the invention is intended to soft tissue augmentation.

The target tissue may be skin but also gingival tissue.

More particularly, the present method may be efficiently used (i) for preventing and/or treating the surface appearance of the skin.

The present method may thus advantageously be used (ii) to prevent and/or treat cutaneous signs of chronological aging and/or induced by external factors such as stress, air pollution, tobacco or prolonged exposure to ultraviolet (UV) exposure, (iii) to prevent and/or treat impaired surface appearance of the skin, (iv) to prevent and/or treat impaired viscoelastic or biomechanical properties of the skin and/or (v) for the long-lasting filling of volume defects of the skin, and in particular the filling of wrinkles.

Furthermore, the method of the invention may be advantageously also used for treating sites of deficiencies and defects in gingival architecture and contour and bony tissue such as occur with teeth loss, increase in age, periodontal disease and disorders, periodontal trauma and after tooth implants, for the enhancement of fit and function of dental prosthetics including but not limited to implants, crown, bridges . . . .

According to another embodiment, the method of the invention is also useful for cartilage regeneration.

According to another embodiment, the method of the invention may be used as a treatment for arthritis.

At last, the hyaluronic acid is a thick transparent liquid similar to the natural fluid located in eyes. Accordingly, it is already proposed for maintaining eyes fluid volume during surgery. Thus the method of the invention is also useful in most ophthalmic intraocular surgeries, including cataract extraction, Intraocular Lens (IOL) insertion and removal, corneal surgery, glaucoma surgery, trauma surgery, ocular plastic surgery and muscle surgery.

According to a second aspect, the invention relates to a sterile and injectable composition, more particularly a soft tissue filler composition, comprising an effective amount of at least hyaluronic acid or a salt thereof and including an effective amount of at least mepivacaine or a salt thereof as anesthetic agent.

Finally, according to another aspect, the invention relates to a method of preparing a sterile and injectable composition, more particularly a soft tissue filler composition, the method comprising at least the steps of:

a) providing at least one gel of a hyaluronic acid or a salt thereof, said hyaluronic acid being selected under a crosslinked hyaluronic acid form, a non-crosslinked hyaluronic acid form or a mixture thereof;

b) adding to said gel of hyaluronic acid at least mepivacaine or a salt thereof as anesthetic agent; and c) sterilizing the mixture obtained in step b).

DETAILED DESCRIPTION OF THE PREFERRED EMBODIMENT

According to a first aspect, the invention relates to a method comprising at least the administering by injection to a patient in need thereof:

(a) at least an efficient amount of hyaluronic acid or a salt thereof; and (b) at least an efficient amount of mepivacaine or a salt thereof as anesthetic agent, said mepivacaine being administered before or concurrently with the hyaluronic acid.

The inventors have indeed found that a method according to the invention may constitute a viable alternative to current methods for in particular preventing and/or treating the surface appearance of the skin which consider the implementation of hyaluronic acid with lidocaine but also (i) for treating sites of deficiencies and defects in gingival architecture and contour and bony tissue, (ii) for ophthalmic intraocular surgeries, (ii) for the regeneration of the cartilage and (iv) in the treatment of arthritis.

Firstly, in contrast to lidocaine, mepivacaine do not displays significant vasodilatory properties than lidocaine.

Furthermore, mepivacaine has a pKa of 7.6 whereas lidocaine has a pKa of 7.9.

Therefore, mepivacaine having a pKa lower than lidocaine, it displays a better lipid solubility which improves its diffusion through lipid barriers. Therefore, due to the fact that mepivacaine may be absorbed more rapidly than lidocaine, mepivacaine is therefore appropriate to better prevent a painful sensation during the injection.

But above all, the inventors have unexpectedly observed than a filler compositions according to the invention, i.e including mepivacaine as anesthetic agent, may be sterilized without significantly affecting the stability of the gel of hyaluronic acid.

It is indeed known than the gels of hyaluronic acid are particularly sensible to the heat treatment like required for their sterilization and that this low stability may be increased by the presence of further materials like the anesthetic agent. Unexpectedly, this undesirable phenomenon is significantly lowered with mepicavaine comparatively to lidocaine, as shown in the following examples 1 and 2. In addition, the inventors have shown that a composition according to the invention further complies with the requirements in terms of stability in time, as hereinafter shown in example 3.

According to the inventors, the manifestation of these above-mentioned advantageous effects within soft tissue filler compositions comprising hyaluronic acid was not known.

Preferably, the hyaluronic acid or a salt thereof is administered concurrently with the mepivacaine or a salt thereof.

Preferably, the administering by injection is an intraepidermal and/or intradermal and/or subcutaneous injection. However it may be also administered by a gingival, articular and intraocular road.

Hyaluronic Acid

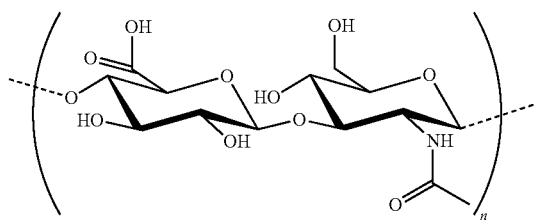

As above-mentioned hyaluronic acid (also called hyaluronan or hyaluronate) is a linear non-sulfated glycosaminoglycan composed of repeating units of D-glucuronic acid and N-acetyl-D-glucosamine (Tammi R., Agren U M., Tuhkanen A L., Tammi M. Hyaluronan metabolism in skin. Progress in Histochemistry & Cytochemistry 29 (2): 1.-81, 1994).

In the skin, hyaluronic acid is primarily synthesized by dermal fibroblasts and epidermal keratinocytes (Tammi R., cited above). Through its residues bearing a negative charge, hyaluronic acid acts as a water pump for maintaining the elasticity of the skin.

As above-mentioned, the present invention considers the implementation of hyaluronic acid as such but also a salt thereof.

Therefore, the hyaluronic acid in accordance with the invention may be more particularly chosen from physiologically acceptable salts such as the sodium salt, the potassium salt, the zinc salt, the silver salt and mixtures thereof, preferably the sodium salt.

Preferably, the hyaluronic acid according to the invention has a high average molecular weight, preferably ranging from 50 000 to 10 000 000 Daltons, preferably from 500 000 to 4 000 000 daltons.

One particularly preferred salt of hyaluronic acid is sodium hyaluronate (NaHA).

As above-mentioned, hyaluronic acid is administered by injection in an effective amount.

An "effective amount" of hyaluronic acid is an appropriate amount to obtain the desired technical effect, notably to have a visible result on the surface appearance of the skin. In particular, an effective amount of hyaluronic acid is an appropriate amount of hyaluronic acid for a good filling of volume defects of the skin, and in particular the filling of wrinkles.

Adjusting the amount of hyaluronic acid falls within the competence of a person skilled in the art.

Advantageously, the hyaluronic acid or a salt thereof in a method according to the invention is present in a solution.

In this regard, an effective amount of hyaluronic acid may range from 0.1 to 5% by weight, preferably from 1 to 3% by weight, relative to the total weight of said solution comprising the hyaluronic acid or a salt thereof.

According to a particular embodiment, the hyaluronic acid may be present under an uncrosslinked form.

For the purpose of the present invention, the term "uncrosslinked" or "non-crosslinked" is understood in the context of the present invention to mean a gel of hyaluronic acid which is not crosslinked or slightly crosslinked, that is to say a gel having a phase-shift angle δ, measured under dynamic rheology conditions at 1 Hz, that is greater than 40° when subjected to a stress above 1 Pa.

According to another particular embodiment, the hyaluronic acid may be present under a crosslinked form.

According to another particular embodiment, the hyaluronic acid may be present under crosslinked and non-crosslinked forms.

In this regard, the weight ratio "crosslinked hyaluronic acid/non-crosslinked hyaluronic acid" is preferably greater than 1.

According to a particular embodiment, the solution comprising the hyaluronic acid and being intended to be administered may comprise:
from 50% to 99% by weight, more preferably 70% to 95% by weight of hyaluronic acid present in the form of a crosslinked gel,
from 1% to 50% by weight, preferably 5% to 30% by weight, of hyaluronic acid present in the free form or a physiologically acceptable salt thereof,
the ratio between the weight of the crosslinked hyaluronic acid gel and the weight of the free hyaluronic acid being between 1:1 and 1:0.02.

When the hyaluronic acid is crosslinked, said crosslinked hyaluronic acid has preferably a degree of modification ranging from 0.1 to 20%, preferably from 0.4 to 10%.

By "degree of modification" is meant, in the sense of the present invention, the ratio between the number of moles of crosslinking agent attached to the hyaluronic acid and the number of moles of hyaluronic acid forming said crosslinked hyaluronic acid gel. This value may be measured by a NMR analysis 1D 1H of the crosslinked gel.

By "number of moles of hyaluronic acid" is meant the number of moles of repeating disaccharide units of the hyaluronic acid, a disaccharide unit being composed of D-glucuronic acid and D-N-acetylglucosamine linked together by alternated beta-1,4 and beta-1,3 glycosidic bonds.

This degree of modification may be notably appreciated as disclosed herein after.

Thus, the characterizing of the degree of modification of the hyaluronic acid is carried out by spectroscopy by NMR (spectrometer Bruker Avance 1 operating at 400 MHz ($^1$H)).

For BDDE, the degree of modification is obtained by integrating the signal of $^1$H NMR N-acetyl group (δ≈2 ppm) present in the hyaluronic acid and a signal present in the crosslinking agent (two —CH2- groups, δ≈1.6 ppm). The ratio of integrals of these two signals (crosslinking agent/NaHA) relates to the degree of modification, after correcting the number of protons attached to each signal:

$$\text{Degree of modification} = \frac{\left[\frac{\text{Integral } \delta_H 1.6}{4}\right]}{\left[\frac{\text{Integral } \delta_H 2.0}{3}\right]}$$

Crosslinking Agent

The term "crosslinking agent" is understood to mean any compound capable of inducing a crosslinking between the various chains of the hyaluronic acid.

The choice of this crosslinking agent clearly falls within the competence of a person skilled in the art.

A crosslinking agent in accordance with the invention may be chosen from difunctional or multifunctional epoxy crosslinking agents but also polyamines like for example hexamethylenediamine (HMDA) or endogeneous polyamines.

By "endogenous polyamine" within the meaning of the present invention is meant a polyamine naturally present in living organisms and particularly the human body. As representative of endogenous polyamines, may be especially mentioned those cited in eukaryotes animals, such as the putrescine (or 1,4-diaminobutane), the spermidine (or 1,8-diamino-5-azaoctane) and the spermine (1,12-diamino-5,9-diazadodecane), preferably the spermine.

More particularly, a crosslinking agent according to the present invention may be preferably selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane, an endogenous polyamine, and mixtures thereof.

Preferably, a crosslinking agent according to the invention is 1,4-butanediol diglycidyl ether (BDDE).

In the particular embodiment wherein the crosslinking agent is a polyamine, and more particularly an endogenous polyamine, the coupling reaction with the hyaluronic acid may be carried out in the presence of at least one activator, and the case arising associated with at least one auxiliary coupling.

In this regard, the activator may be selected from water-soluble carbodiimides such as 1-ethyl-3-(3-dimethylaminopropyl)carbodiimide (EDC), 1-ethyl-3-(3-25 trimethylaminopropyl)carbodiimide hydrochloride (ETC), 1-cyclohexyl-3-(2-morpholinoethyl)carbodiimide (CMC) and a salt thereof, and mixtures thereof, preferably is represented by the EDC.

Regarding the coupling auxiliary, when it is present, it may be selected from N-hydroxy succinimide (NHS), N-hydroxybenzotriazole (HOBt), 3,4-dihydro-3-hydroxy-4-oxo-1,2,3-benzotriazole (HOOBt), 1-hydroxy-7-7azabenzotriazole (HAt) and N-hydroxysylfosuccinimide (sulfo NHS), and mixtures thereof, preferably is represented by the HOBt.

The crosslinking agent is implemented in an effective amount.

An "effective amount" of crosslinking agent is an appropriate amount to obtain an appropriate degree of crosslinking of hyaluronic acid.

Adjusting the amount of crosslinking agent falls within the competence of a person skilled in the art.

Advantageously, an effective amount of crosslinking agent may range from 0.05 to 15% by weight relative to the total weight of the hyaluronic acid or a salt thereof.

Advantageously, when the hyaluronic acid is crosslinked, and when the crosslinking agent is BDDE, the amount in mole ratio of nBDDE/n hyaluronic acid may range between 0.01 and 0.5, preferably between 0.04 and 0.25.

Anesthetic Agent

An anesthetic agent according to the present invention has the particular advantage to reduce or eliminate the pain sensation experienced by the patient during and/or following the injection.

Moreover, an anesthetic agent according to the present invention is chosen among compounds which do not raise risk of incompatibility with other compounds used in a composition according to the invention, especially with hyaluronic acid.

As above-mentioned, an anesthetic agent according to the present invention is mepivacaine, or a salt thereof.

The mepivacaine is a local anesthetic of the amino-amids family of the formula (I):

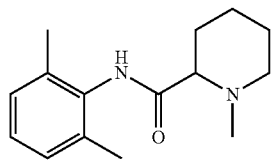

(I)

The mepivacaine is notably sold under the name Carbocaine® by the company Cook-Waite.

The mepivacaine is a molecule having a good stability. Its main degradation product is 2,6-dimethylaniline. Mepivacaine is a molecule containing a chiral center (asymmetric carbon). Thus, there are the R and S enantiomers. In the following examples, it is considered the racemic mixture of the two forms of mepivacaine.

Preferably, the mepivacaine is under a salt form, and more particularly the salt of mepivacaine is chlorhydrate mepivacaine.

As above-mentioned, the mepivacaine or a salt thereof is administered by injection in an effective amount.

An "effective amount" of mepivacaine or a salt thereof is an appropriate amount to effectively reduce or eliminate the pain sensation experienced by the patient during and/or following the injection.

Adjusting the amount of mepivacaine or a salt thereof falls within the competence of a person skilled in the art.

Advantageously, the mepivacaine or a salt thereof in a method according to the invention is present in a solution.

In this regard, an effective amount of the mepivacaine or a salt thereof may range from 0.05 to 3% by weight relative to the weight of the solution comprising said mepivacaine or a salt thereof.

The method may further comprises the administration, the case arising joint to the mepivacaine, of at least one additional anesthetic agent or a salt thereof different from the mepivacaine.

This further anesthetic agent may be in particular selected from ambucaïne, amolanone, amylocaine, benoxinate, benzocaine, betoxycaine, biphénamine, bupivacaine, butacaine, butamben, butanilicaine, butethamine, betoxycaïne, carticaïne, chloroprocaine, cocaethylene, cocaine, cyclométhycaïne, dibucaine, diméthysoquine, dimethocaine, diperodone, dycyclonine, ecgonidine, ecgonine, ethyl chloride, etidocaine, beta-eucaine, euprocine fenalcomine, formocaine, hexylcaine, hydroxytétracaïne, isobutyl p-aminobenzoate, leucinocaïne mesylate, levoxadrol, lidocaine, meprylcaïne, metabutoxycaïne, methyl chloride, myrtecaïne, naepaïne, octacaïne, orthocaïne, oxethazaine, parethoxycaine, phénacaïne, phenol, piperocaine, piridocaïne, polidocanol, pramoxine, prilocaine, procaine, propanocaine, proparacaine, propipocaïne, propoxycaine, pseudococaïne, pyrrocaine, ropivacaine, salicyl alcohol, tetracaine, tolycaïne, trimécïne, zolamine, or a salt thereof, and a mixture thereof.

Preferably, this additional anesthetic agent is lidocaine or a salt thereof.

According to a first embodiment, the additional anesthetic agent is administered alone, previous to the hyaluronic acid and the mepivacaine or a salt thereof.

According to a second embodiment, the additional anesthetic agent is administered together with the mepivacaine or a salt thereof, previous to the hyaluronic acid or a salt thereof.

According to a third embodiment, the additional anesthetic agent is administered together with the mepivacaine or a salt thereof and the hyaluronic acid or a salt thereof.

In the specific embodiment where both anesthetic agents are contained in a same composition, they may be present therein in a ratio "mepivacaine/lidocaine" 1:1, preferably a ratio 1:0.1.

Balanced Salt Solution

According to a particular embodiment, the method according to the invention may further comprise at least a step of administering by injection to said patient of (c) at least a balanced salt solution, concurrently with said hyaluronic acid and/or mepivacaine, preferably with mepivacaine.

The implementation of this balanced salt solution is particularly interesting in that it allows still reducing the injection pain (see Farley J. S. et al., Regional Anesthesia A., 1994, Vol. 19: 48).

Preferably, said balanced salt solution is a phosphate buffered saline, and more particularly is a phosphate buffered saline and particularly a $KH_2PO_4/K_2HPO_4$ saline buffer.

According to a particular embodiment, said balanced salt solution may further comprise at least one compound selected from the group consisting of an alpha-lipoic acid; N-Acétyl-L-cysteine; reduced glutathion; amino acid such as L-Arginine, L-Isoleucine, L-Leucine, monohydrated L-Lysine, Glycine, L-Valine, L-Threonine, L-Proline; pyridoxine Hydrochloride; dehydrated zinc acetate; pentahydrates copper sulphate, and mixture thereof.

Composition According to the Invention

As above-mentioned, the present invention also relates to a sterile and injectable composition, in particular a soft filler composition, comprising an effective amount of at least hyaluronic acid or a salt thereof and including an effective amount of at least mepivacaine or a salt thereof as anesthetic agent.

By "sterile", in the sense of the present invention, is meant an environment capable of guaranteeing to the considered compounds in a composition according to the invention safety requirements for the administration routes such as above-mentioned, notably into or through the skin. Indeed, for obvious reasons, it is essential that a composition according to the invention be devoid of any contaminant body capable of initiating an undesirable side reaction at the host organism.

The hyaluronic acid, the crosslinking agent, and the anesthetic agent(s) are such as above-mentioned.

Regarding the hyaluronic acid, a composition according to the invention may comprise from 0.1 to 5% by weight, preferably from 1 to 3% by weight of hyaluronic acid, relative to the total weight of said composition.

According to a particular embodiment, as above-mentioned, the hyaluronic acid may be present in crosslinked and non-crosslinked forms.

In this regard, the ratio "crosslinked hyaluronic acid/non-crosslinked hyaluronic acid" is preferably greater than 1.

More particularly, a composition according to the invention may comprise:
- from 50% to 99% by weight, more preferably 70% to 95% by weight of hyaluronic acid present in the form of a crosslinked gel,
- from 1% to 50% by weight, preferably 5% to 30% by weight of hyaluronic acid present in a non-crosslinked form,
- the ratio between the weight of the crosslinked hyaluronic acid gel and the weight of the non-crosslinked hyaluronic acid being between 1:1 and 1:0.02.

Regarding the anesthetic agent(s), a composition according to the invention may comprise from 0.01% to 5% by weight, preferably from 0.05% to 3% by weight of anesthetic agent(s), based on the total weight of said composition.

By its injectable character, a composition according to the invention necessarily comprises a physiologically acceptable medium.

A "physiologically acceptable medium" means a medium devoid of toxicity and compatible with the injection and/or the application of the composition such as considered in the present invention.

The composition may comprise a solvent or a mixture of physiologically acceptable solvents.

The composition may comprise a physiologically acceptable aqueous medium.

As an aqueous medium suitable for the invention, may be for example mentioned water.

As isotonic agents suitable for the preparation of a composition according to the invention, it may be mentioned sugars and sodium chloride.

According to a particular embodiment, a composition according to the invention may further comprise at least a balanced salt solution such as above-mentioned.

According to a particular embodiment, a composition according to the invention may further comprise at least one compound selected from the group consisting of an alpha-lipoic acid; N-Acétyl-L-cysteine; reduced glutathion; amino acid such as L-Arginine, L-Isoleucine, L-Leucine, monohydrated L-Lysine, Glycine, L-Valine, L-Threonine, L-Proline; pyridoxine Hydrochloride; dehydrated zinc acetate; pentahydrates copper sulphate, and mixture thereof.

A composition according to the invention may comprise, in addition to the above-mentioned compounds, at least one additional compound compatible with use in the field of soft tissue filler composition compositions.

In this regard, additional compounds which may be implemented in a composition according to the invention may be chosen from copper salt, alpha-lipoic acid, acetylated derivative of cysteine or mixture thereof.

The amounts of these additional compounds depend on the nature of the compound in question, the desired effect, and the destination of the composition according to the invention.

These parameters belong to the general skill of the art.

A composition further comprising at least one copper salt may preferably comprises said copper salt in an amount ranging from 0.1 to 50 ppm based on the total weight of said composition.

A composition further comprising at least one alpha-lipoic acid preferably comprises said alpha-lipoic acid in an amount ranging from 0.5 to 10,000 ppm, preferably from 5 to 100 ppm of alpha-lipoic acid, based on the total weight of said composition.

A composition further comprising at least one acetylated derivative of cysteine preferably comprises said acetylated derivative of cysteine in an amount ranging from 0.5 to 10,000 ppm based on the total weight of said composition.

Among the other additional compounds which may be used in the present invention, may be mentioned antioxidants, amino acids, vitamins, minerals, nucleic acids, co-enzymes, adrenal derivatives, and mixtures thereof, said additional compounds being distinct from those indicated above.

As an antioxidant, it may be mentioned glutathione, ellagic acid, spermine, resveratrol, retinol, L-carnitine, polyols, polyphenols, flavonols, theaflavins, catechins, caffeine, ubiquinol, ubiquinone, and mixture thereof.

As amino acid, there may be mentioned arginine, isoleucine, leucine, lysine, glycine, valine, threonine, proline, methionine, histidine, phenylalanine, tryptophan, and mixture thereof.

As vitamins and their derivatives, may be mentioned vitamins E, A, C, B, especially vitamins B6, B8, B4, B5, B9, B7, B12, and pyridoxine better.

As minerals, mention may in particular be made of zinc salts, magnesium salts, calcium salts, potassium salts, manganese salts, sodium salts, and mixtures thereof.

As nucleic acids, may be mentioned in particular the derivatives of adenosine, cytidine, guanosine, thymidine, the cytodine and mixture thereof.

As co-enzymes, may be cited coenzyme Q10, CoA, NAD, NADP, and mixtures thereof.

As an adrenaline derivatives, may be mentioned adrenaline, noradrenaline.

In addition, a composition according to the invention may further comprise any excipient commonly used in the technical field, such as for example mono- and/or di-hydrated dihydrogenophosphate sodium and sodium chloride, in physiological concentrations.

The amounts of additional active agents and/or excipients of course depend on the nature of the compound in question, the desired effect, and the destination of the composition according to the invention.

According to a particular embodiment, a composition according to the invention may have a complex viscosity $\eta^*$ of between about 5 Pa*s and about 450 Pa*s when measured at about 1 Hz.

According to a particular embodiment, a composition according to the invention made up of crosslinked hyaluronic acid may have a viscosity between 200 and 2000 Pa·s, preferably between 1000 and 1800 Pa·s.

The viscoelastic properties of a composition according to the invention may be measured using a rheometer (notably Haake RS6000) with a cone/plate geometry (1° cone angle/35 mm diameter plate). A strain scan is carried out and the elastic modulus G' (in Pa) and the phase-shift angle $\delta$ (in °) are measured for a stress of 5 Pa.

Method for Preparing a Sterile and Injectable Composition According to the Invention As above-mentioned, the present invention also relates to a method of preparing a sterile and injectable composition, more particularly a soft tissue filler composition, the method comprising at least the steps of:
a) providing at least one gel of a hyaluronic acid or a salt thereof, said hyaluronic acid being selected under a crosslinked hyaluronic acid form, a non-crosslinked hyaluronic acid form or a mixture thereof;
b) adding to said gel of hyaluronic acid at least mepivacaine or a salt thereof as anesthetic agent; and
c) sterilizing the mixture obtained in step b).

According to a preferred embodiment, the mepivacaine or a salt thereof is added to an injectable form of hyaluronic acid.

In other words, the gel of hyaluronic acid considered in step a) already exhibits a concentration in hyaluronic acid, in crosslinking agent residues if presents, and physiological and/or pH conditions which are compatible with an injectable use, in particular in the fields of the applications considered above.

By this way, the risks affecting the stability of the hyaluronic acid in the mixture hyaluronic acid and mepivacaine by imposing additional purification steps, such as above-defined, are significantly reduced.

The mixture advantageously undergoes only one sterilization step. This step is preferably carried out on the mixture already packaged in its delivery device, usually a syringe, as herein after defined.

Advantageously, the sterilization step can be performed by thermal means.

Advantageously, the sterilization is carried out at a temperature ranging from 120 to 140° C.

In particular, the sterilization step can be performed in an autoclave (moist heat) T° C.≥121° C., to obtain a F0>15 (sterilizing value).

In this regard, and as above-mentioned, a composition according to the invention is particularly advantageous in that it displays a very interesting high resistance to this sterilization step.

Indeed, as shown in the examples 1 and 2, the loss of G' generated by sterilization for a composition according to the invention is less than for a composition comprising lidocaine instead of mepivacaine.

According to a particular embodiment, the method for preparing a gel of hyaluronic acid according to the invention may further comprise a step d) consisting of adding an additional anesthetic agent or a salt thereof, different from the mepivacaine or a salt thereof, such as above-mentioned, preferably lidocaine or a salt thereof, said step d) being carried out before, simultaneously and/or after the step b).

When the gel considered in step a) comprises a crosslinked hyaluronic acid form, this last may be obtained beforehand from an uncrosslinked form of hyaluronic acid.

The reticulation may be performed by a conventional way with at least one crosslinking agent, such above-mentioned.

The aqueous mixture comprising the crosslinking agent and the hyaluronic acid to crosslink is advantageously homogenized before performing the crosslinking.

The purpose of this operation is more particularly for the hyaluronic acid or a salt thereof in the aqueous medium to be hydrated and homogenized perfectly and thus to help to optimize the properties of the gel of hyaluronic acid expected. This step of homogenization is more important when the hyaluronic acid has a high molecular weight, because the hydration of such a compound tends to result in the formation of a high-viscosity solution within which the appearance of agglomerates is commonly observed.

The purpose of this operation is also intended to homogenize perfectly the crosslinking agent within the mixture so as to subsequently assure a homogeneous crosslinking reaction.

The homogenization is considered to be satisfactory when the solution obtained is uniformly coloured, with no agglomerates, and has a uniform viscosity. The homogenization may advantageously be carried out under mild operating conditions so as to prevent degradation of the hyaluronic acid chains.

The duration of this homogenization step depends on the nature of the hyaluronic acid or a salt thereof, and more particularly the molecular weight and the concentration thereof, on the operation conditions within the aqueous medium and on the homogenizing device used, generally a device which allows a soft mechanical agitation.

Preferably, a homogenization step may take place over a time of less than 200 minutes, preferably less than 150 minutes, or even between 15 and 100 minutes.

The purpose of the crosslinking reaction is to create bridges between the hyaluronic acid chains making it possible to obtain a dense solid three-dimensional network from a viscous solution.

The particular conditions to be adopted in order to stimulate the crosslinking reaction may depend on the molecular weight of the hyaluronic acid, on the aqueous medium and on the nature of the crosslinking agent. In general, this reticulation may be achieved by bringing the mixture comprising the non crosslinked hyaluronic acid and at least one crosslinking agent as above-mentioned, into contact with a triggering element, or stimulant, such as, for example by heating or exposure to UV, or even by bringing said mixture into contact with a material of the catalyst type.

The choice of such a triggering element falls within the general knowledge of a person skilled in the art.

In the context of the present invention, this triggering element is advantageously represented by an increase in temperature imposed on the mixture "non-crosslinked hyaluronic acid/aqueous medium/crosslinking agent".

A particularly suitable temperature for the crosslinking reaction is between 35° C. and 60° C., preferably between 45 and 55° C., and better still between 48 and 52° C.

The degree of crosslinking also depends on the crosslinking time and of the temperature imposed on the mixture "non-crosslinked hyaluronic acid/aqueous medium/crosslinking agent". The longer the time is, the higher the degree of crosslinking will be, with however an optimum not to be exceeded without running the risk of degrading the hyaluronic acid.

Thus, at a temperature ranging from 35° C. and 60° C., the crosslinking reaction may be carried out over a time ranging from 30 to 300 minutes, preferably 100 to 200 minutes, and better still 150 to 190 minutes.

Preferably, the crosslinking conditions are adjusted to obtain a degree of crosslinking such that the gel of crosslinked hyaluronic acid formed is a viscous, viscoelastic gel, or even a solid gel.

Stopping the crosslinking reaction requires exposing the crosslinked gel or, during crosslinking, even the receptacle containing it, to conditions propitious for stopping the crosslinking or else to conditions capable of stopping the formation of bonds between the various hyaluronic acid chains.

For example, with regard to the thermal conditions that will be applied to stimulate the crosslinking process, the crosslinking may be stopped:
- by simply removing the receptacle from the thermostatted bath and cooling it until it returns to room temperature;
- by placing the receptacle in a bath of cold water, preferably at a temperature below room temperature, until the temperature within said receptacle is close to room temperature; or even
- by extracting the gel from said receptacle.

According to a particular embodiment, the homogenization and crosslinking may be carried out within a hermetic cavity delimited at least partially by a deformable wall, preferably made within a deformable pouch, which may be deformed at least manually by palpation, such as described notably in WO 2010/131175.

The gel obtained at the end of the crosslinking step cannot in general be injected directly, in particular because of its high hyaluronic acid concentration and/or of the possible presence of crosslinking agent residues or else because of its physiological and/or pH conditions incompatible with use in the fields of applications considered above.

Furthermore, some gels may especially have too high a stiffness to be injected as such into a patient. Therefore, several additional steps, known to those skilled in the art, can be carried out to obtain an injectable hydrogel. More particularly, a step of neutralizing and expanding this gel is required in order to give it its implant qualities. The chains of the hyaluronic acid network are then stretched and hydrated, while the pH is brought to that of the dermis.

A step of protecting and redensifying the gel can also be carried out for further improving the qualities of the implant, according to the know-how of a person skilled in the art. The gel must be physiologically formulated by virtue of the presence of salts in equivalent amounts to those of the medium injected.

For even higher purity, an additional purification step may also be carried out.

Advantageously, the mepivacaine or salt thereof and, the case arising, additional anesthetic agent(s), is/are added at the end of this protocol of preparation of an injectable form of hyaluronic acid, just before the step of sterilization, such as above-defined.

According to a particular embodiment, the hydrogel added of mepicacaine and optionally of additional anesthetic agent(s), may be used to fill syringes under controlled atmosphere conditions, said syringes then possibly undergoing a sterilization step, preferably a thermal sterilization step such as above-defined.

Administration of the Composition

A composition according to the invention can be injected using any of the known methods in the art.

Particularly, a composition of the invention may be administered by means of an injection device suitable for intraepidermal and/or intradermally and/or subcutaneously.

A composition of the invention may also be administered by means of an injection device suitable for gingival, articular and/or intraocular regions.

The injection device, notably when a composition of the invention is administered by means of an injection device suitable for intraepidermal and/or intradermally and/or subcutaneously, may be selected from a syringe, a set of microsyringes, a laser device, a hydraulic device, an injection gun, a needleless injection device, a rolling with microneedles.

Preferably, the injection device may be selected from a syringe or a set of microsyringe.

In an alternative embodiment, the injection device can be adapted to the technique of mesotherapy.

Mesotherapy is a treatment technique by intraepidermal and/or intradermally and/or subcutaneously active(s) product(s).

The administration intraepidermal and/or intradermally and/or subcutaneously according to the invention is to inject a composition of the invention in an epidermal region, dermo-epidermal and/or dermal.

The injection device may comprise any conventionally used injection such as hypodermic needle or cannula.

A needle or a cannula according to the invention can have a diameter ranging between 18 and 34 G, preferably 25 to 32 G, and a length varying from 4 to 70 mm, preferably 4 to 25 mm.

The needle or cannula is preferably disposable.

Advantageously, the needle or cannula is associated with a syringe or other device capable of delivering through the needle or cannula said injectable composition.

According to one embodiment, a catheter may be inserted between the needle/cannula and syringe.

In known manner, the syringe can be operated manually by the practitioner or by a syringe holder as guns.

Throughout the description, including the claims, the expression "comprising a" should be understood as being synonymous with "comprising at least one" unless specifically stated otherwise.

The expressions "between . . . and . . . " and "ranging from . . . to . . . " should be understood to mean that the limits are inclusive, unless specified otherwise.

The following examples and figures are presented by way of non-limiting illustration of the invention.

EXAMPLES

Material and Method:

The protocol herein after defined regarding the measure of the viscoelastic properties of a composition apply for the following examples.

The viscoelastic properties of a composition are measured using a rheometer (Haake RS6000) with a cone/plate geometry (1° cone angle/35 mm diameter plate). A strain scan is carried out and the elastic modulus G' (in Pa) and the phase-shift angle δ (in °) are measured for a stress of 5 Pa.

Example 1: Protocol of Preparing a Composition According to the Invention Implementing a Non Crosslinked Hyaluronic Acid and Analysis Regarding its Stability to the Sterilization 3 g of hyaluronic acid (1.5 MDa) and 197 g of a phosphate buffer (as defined in FR 2 979 539) are mixed.

The protocol of preparing is as follows:

1. tridimensional homogenization of the mixture "hyaluronic acid+phosphate buffer" at room temperature in an airtight container (Nalgene jar) for a minimum of 20 hours;

2. separating the obtained non-crosslinked gel into 2 equivalent fractions (called hereinafter fractions A1 and A2);

3. regarding fraction A1, adding to gel 1% by weight of a solution of mepivacaine (30% by weight in phosphate buffer medium) and 0.4% by weight of a solution of NaOH 1%; or 4. regarding fraction A2, adding to gel 1% by weight of a solution of lidocaine (30% by weight in phosphate buffer medium) and 0.4% by weight of a solution of NaOH 1%; and 5. homogenization, packaging in syringes 1 mL for injection, and autoclaving (F0>15).

Results:

Tables below gives the values of the elastic moduli G' (in Pa) of the hydrogels obtained and of the extrusion force F(N).

|  | Fraction A1 | Dynamic oscillatory rheology | | F(N) at 12.5 mm/min Ser Schott 1 mL |
|---|---|---|---|---|
|  |  | F = 5 Hz G' (Pa) | F = 1 Hz G' (Pa) | Needle TSK HPC 30 G: 120347 |
| Mepivacaine 0.3% | Non-sterilized | 103.3 | 36.3 | 9 |
|  | Sterilized | 45.0 | 9.6 | 9 |
|  | Loss on sterilization (in %) | 56.4 | 73.5 |  |

The loss in sterilization for G' at F=5 Hz is calculated as follows: (103.3−45.0)/103.3=56.4 (en %)

|  | Fraction A2 | Dynamic oscillatory rheology | | F(N) at 12.5 mm/min Ser Schott 1 mL |
|---|---|---|---|---|
|  |  | F = 5 Hz G' (Pa) | F = 1 Hz G' (Pa) | Needle TSK HPC 30 G: 120347 |
| Lidocaine 0.3% | Non-sterilized | 105.9 | 37.4 | 9 |
|  | Sterilized | 36.7 | 7.0 | 9 |
|  | Loss on sterilization (in %) | 65.4 | 81.2 |  |

In view of the above, it therefore appears that the stability to the sterilization step of a composition comprising uncrosslinked hyaluronic acid is at least equivalent with mepivacaine than with lidocaine.

The results are even significantly better with mepivacaine.

Example 2: Protocol of Preparing a Composition According to the Invention Implementing Crosslinked and Non Crosslinked Hyaluronic Acid and Analysis Regarding its Stability to the Sterilization 8 g of hyaluronic acid (4 MDa), 58.7 g of sodium hydroxide (NaOH) 1% and 0.6 g of butanediol diglycidyl ether (BDDE) are implemented. The crosslinking reaction is induced by an incubation for 3 hours at 52° C.

The protocol of preparing is as follows:
1. Homogenization of the mixture "hyaluronic acid+NaOH 1%" at room temperature in an airtight and deformable container (pouch such as considered in the patent application WO 2010/131175) during about 1H30 so as to obtain a perfectly homogeneous viscous solution;
2. Adding the crosslinking agent (BDDE) into the receptacle and new homogenization at room temperature for about 20 min;
3. Incubation for 3 hours at 52° C. of the receptacle containing the viscous solution of "hyaluronic acid/sodium hydroxide 1%/BDDE" so as to initiate the crosslinking step;
4. Neutralization, swelling and homogenizing the obtained solid (solution of crosslinked hyaluronic acid) in a phosphate buffer (as defined in FR 2 979 539), and adding a non-crosslinked gel containing 4 g of HA 4 MDa and 668 g of supplemented phosphate buffer, so as to obtain a hydrogel having 11 mg/g in hyaluronic acid, at pH around neutrality;
5. Purification by dialysis during 48 hours, and then collecting the purified gel in a tank homogenization;
6. Sieving of the whole gel (230 μm);
7. Separation of the collected gel into two fractions (Fraction B1 and B2);
8. Incorporation to the gel of 1% by weight of a solution of mepivacaine (30% by weight in medium phosphate buffer) and of 0.4% by weight of a solution of NaOH 1% (=Fraction B1);
9. Incorporation to the gel of 1% by weight of a solution of lidocaine (30% by weight in medium phosphate buffer) and of 0.4% by weight of a solution of NaOH 1% (=Fraction B2);
10. Homogenization, packaging in syringes 1 mL for injection and sterilization.

Results:

Tables below gives the values of the elastic modulus G' (in Pa) of the hydrogels obtained and of the extrusion force F(N).

|  | Fraction B1 | Dynamic oscillatory rheology F = 1 Hz G' (Pa) | F(N) at 12.5 mm/min Ser Schott 1 mL Needle TSK HPC 30 G: 120347 |
|---|---|---|---|
| Mepivacaine 0.3% | Non-sterilized | 20.4 | 10 |
|  | Sterilized | 8.1 | 10 |
|  | Loss on sterilization (in %) | 60.3 |  |

|  | Fraction B2 | Dynamic oscillatory rheology F = 1 Hz G' (Pa) | F(N) at 12.5 mm/min Ser Schott 1 mL Needle TSK HPC 30 G: 120347 |
|---|---|---|---|
| Lidocaine 0.3 0.3% | Non-sterilized | 19.2 | 10 |
|  | Sterilized | 6.2 | 10 |
|  | Loss on sterilization (in %) | 67.6 |  |

The loss in sterilization is calculated as displayed in example 1.

In view of the above, it therefore appears that the stability to the sterilization step of a composition comprising crosslinked and uncrosslinked hyaluronic acid is at least equivalent with mepivacaine than with lidocaine.

The results are even better with mepivacaine.

Example 3: Protocol of Preparing a Composition According to the Invention Implementing Crosslinked and Non Crosslinked Hyaluronic Acid and Analysis Regarding its Stability in Time 10 g of hyaluronic acid (1.5 MDa) 73 g of sodium hydroxide 1% and 0.9 g of butanediol diglycidyl ether (BDDE) are mixed. Then, the crosslinking reaction is induced by incubation for 3 hours at 52° C.

The preparation procedure is as follows:

1. homogenizing the mixture at room temperature "hyaluronic acid+sodium hydroxide 1%, in an airtight and deformable container (pocket) for about 1H30 to obtain a perfectly homogeneous viscous solution;
2. adding the crosslinking agent (BDDE) into the container and further homogenization at room temperature for about 20 min;
3. incubation for 3 hours at 52° C. of the receptacle containing the viscous solution of hyaluronic acid/sodium hydroxide 1%/BDDE so as to initiate the crosslinking step;
4. neutralization, swelling and homogenizing the obtained solid (solution of crosslinked hyaluronic acid) in a phosphate buffer containing 2 g of non-crosslinked hyaluronic acid (1.5 MDa), so as to obtain a hydrogel at 25 mg/g of hyaluronic acid at pH close to neutrality;
5. purification by dialysis (during 48 hours), and then collecting the purified gel in a degassing vessel/homogenization;
6. incorporation in the gel of 1% by weight of a solution of mepivacaine (30% by weight in a phosphate buffer medium) and of 0.4% by weight of a NaOH solution 1%;
7. homogenization, degassing, packaging in syringes 1 mL for injection and sterilization (F0>15).

Results:

Table below gives the values of the phase-shift angle δ (°) and the extrusion force.

| Analysis | Rheology amplitude scan (Cone/plate) δ (°) measures at 5 Pa and 1 Hz | Extrusion Force, measured with needle TSK 30G1/2 F (N), at 12.5 mm/min | pH |
|---|---|---|---|
| T0 | 17.8 ± 2.0 | 24.2 ± 2.5 | 7.1 |
| T0 + 19 months | 19.1 ± 2.0 | 23.1 ± 2.5 | 7.1 |

The results obtained 19 months after the date of manufacture of the gel are equivalent to those obtained initially, and thus demonstrate the stability of the gel.

The disclosure of all publications cited above are expressly incorporated herein by reference, each in its entirety, to the same extent as if each were incorporated by reference individually.

The disclosure of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall therebetween.

What is claimed is:

1. A sterile composition for intraepidermal, intradermal, and/or subcutaneous administration comprising:
   an effective amount of hyaluronic acid or a salt thereof, the effective amount of hyaluronic acid or salt thereof ranging from 1 to 3 wt % of the overall weight of the sterile composition,
   mepivacaine or a salt thereof as a first anesthetic agent at a concentration ranging from 0.05 to 3 wt % of an overall weight of the sterile, injectable composition, and
   a balanced salt solution,
   wherein the sterile composition exhibits greater stability over time and/or during heat treatment resulting in sterilization in comparison to the same composition having lidocaine as the anesthetic agent instead of mepivacaine.

2. The sterile composition according to claim 1, wherein the hyaluronic acid comprises crosslinked hyaluronic acids, non-crosslinked hyaluronic acids, or a mixture thereof.

3. The sterile composition according to claim 2, wherein the salt of mepivacaine is chlorhydrate mepivacaine.

4. The sterile composition according to claim 1, further comprising a second anesthetic agent or a salt thereof as a second anesthetic agent, the second anesthetic agent comprises at least one of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquine, dimethocaine, diperodone, dycyclonine, ecgonidine, ecgonine, ethyl chloride, etidocaine, beta-eucaine, euprocine fenalcomine, formocaine, hexylcaine, hydroxytetracaine, isobutyl p-aminobenzoate, leucinocaine mesylate, levoxadrol, lidocaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycane, trimecaine, zolamine, or a salt thereof, or mixtures thereof.

5. The sterile composition according to claim 1, wherein the balanced salt solution is a phosphate saline buffer.

6. The sterile composition according to claim 1, wherein the hyaluronic acid has an average molecular weight ranging from 50,000 to 10,000,000 Daltons.

7. The sterile composition according to claim 1 wherein the hyaluronic acid comprises crosslinked and non-crosslinked hyaluronic acid at a ratio of 1:1 to 1:0.02 of crosslinked to non-crosslinked hyaluronic acid in the single, sterile injectable composition.

8. The sterile composition according to claim 7, wherein mepivacaine or salt thereof is present at a concentration of 0.3 wt % of the overall weight of the single, sterile injectable composition, and the hyaluronic acid or the salt thereof comprises crosslinked hyaluronic acids.

9. The sterile composition according to claim 1, further comprising an additional compound comprising at least one of an antioxidant(s), amino acid(s), vitamin(s), mineral(s), nucleic acid(s), co-enzyme(s), adrenaline, noradrenaline, or mixtures thereof.

10. The sterile composition according to claim 9, wherein the additional compound is an antioxidant.

11. The sterile composition according to claim 10, wherein the antioxidant comprises glutathione, ellagic acid, spermine, resveratrol, retinol, L-carnitine, polyol(s), polyphenol(s), flavonol(s), theaflavin(s), catechin(s), caffeine, ubiquinol, ubiquinone, or mixtures thereof.

12. The sterile composition according to claim 10, wherein the antioxidant is at least one polyol.

13. The sterile composition according to claim 9, wherein the additional compound comprises an antioxidant and an amino acid, the amino acid selected from the group consisting of arginine, isoleucine, leucine, lysine, glycine, valine, threonine, proline, methionine, histidine, phenylalanine, tryptophan, or mixtures thereof.

14. The sterile composition according to claim 9, wherein the additional compound comprises an antioxidant and a vitamin, the vitamin selected from the group consisting of vitamin E, vitamin A, vitamin C, vitamin B, or mixtures thereof.

15. The sterile composition according to claim 9, wherein the additional compound comprises an antioxidant and a mineral, the mineral selected from the group consisting of zinc salts, magnesium salts, calcium salts, potassium salts, manganese salts, sodium salts, or mixtures thereof.

16. The sterile composition according to claim 9, wherein the additional compound comprises an antioxidant and a nucleic acid, the nucleic acid selected from the group consisting of adenosine, cytidine, guanosine, thymidine, and mixtures thereof.

17. The sterile composition according to claim 9, wherein the additional compound comprises an antioxidant and a co-enzyme, the co-enzyme selected from the group consisting of coenzyme Q10, CoA, NAD, NADP, or mixtures thereof.

18. The sterile composition according to claim 1, wherein the hyaluronic acid or a salt thereof comprises hyaluronic acid crosslinked with at least one crosslinker selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane, and mixtures thereof.

19. The sterile composition according to claim 1, wherein the hyaluronic acid or a salt thereof comprises hyaluronic acid crosslinked with 1,4-butanediol diglycidyl ether (BDDE).

* * * * *